United States Patent [19]

Sellstedt et al.

[11] 4,116,960
[45] Sep. 26, 1978

[54] TETRAZOLE-5-CARBOXAMIDE DERIVATIVES

[75] Inventors: John M. Sellstedt, Pottstown; Dieter H. Klaubert, West Chester, both of Pa.

[73] Assignee: American Home Products Corporation, New York, N.Y.

[21] Appl. No.: 726,374

[22] Filed: Sep. 24, 1976

Related U.S. Application Data

[62] Division of Ser. No. 669,570, Mar. 23, 1976, Pat. No. 4,013,647.

[51] Int. Cl.$^2$ .......................................... C07D 403/12
[52] U.S. Cl. .................................. 544/366; 544/331; 544/405; 544/58; 424/250
[58] Field of Search ................................... 260/268 PH

[56] References Cited

U.S. PATENT DOCUMENTS 4,013,647  3/1977  Sellstedt et al. ............... 260/247.2 A Primary Examiner—Donald G. Daus
Assistant Examiner—Jose Tovar
Attorney, Agent, or Firm—Richard K. Jackson

[57] ABSTRACT

Anti-allergic agents of N-aromatic 1H-(or 2H) tetrazole-5-carboxamide derivation present the following formulae:

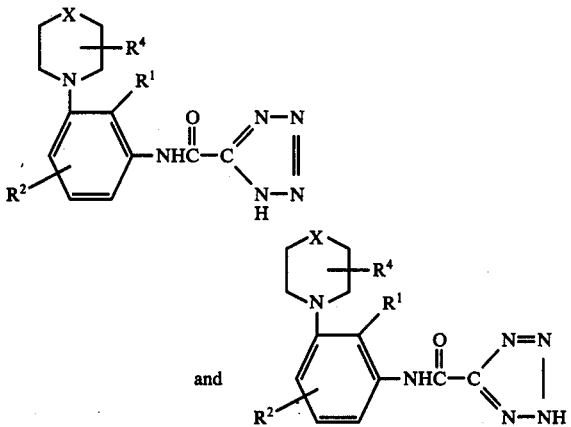

in which
R$^1$ is —CN or —CONH$_2$;
R$^2$ is hydrogen, lower alkyl, lower alkoxy, halo, polyhalo(lower)alkyl, lower alkyl carbonyl or carb(lower)alkoxy;
X is —CH$_2$—, —O—

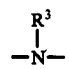

where R$^3$ is lower alkyl and
R$^4$ is hydrogen or lower alkyl;
or a pharmaceutically acceptable salt thereof.

4 Claims, No Drawings

TETRAZOLE-5-CARBOXAMIDE DERIVATIVES

This is a division of application Ser. No. 669,570 filed Mar. 23, 1976, now U.S. Pat. No. 4,013,647, granted Mar. 22, 1977.

BACKGROUND OF THE INVENTION

Atopic immediate sensitivity is the chief manifestation found in animals suffering from bronchial asthma, seasonal pollinosis (e.g. hay fever), allergic rhinitis, urticaria, allergic conjunctivitis, food allergies and anaphylactoid reactions. The substances most frequently responsible for clinically manifest sensitivities are plant pollen, animal feathers and danders, dust, milk and wheat, whether inhaled or ingested. Atopic hypersensitivity is found in man, dog, and other animals. Its occurrance is exceptionally found in the lower animals.

The presence of antibodies associated with atopic hypersensitivity reactions in the host serum is established by the passive sensitization of the skin of a normal recipient, after injection of serum from a sensitized host into a skin site followed by injection of antigen into the same area 24 hours later, resulting in a local hive. This is commonly referred to as the Prausnitz-Kustner (P-K) reaction.

The antibody associated with atopic hypersensitivity possesses distinctive features in that it does not in all forms precipitate with its antigen, fails to pass the placenta from mother to fetus, has special affinity for the skin, frequently lacks specificity toward an individual antigenic factor and is usually labile at about 56° C. after 2 hours.

The homocytotropic antibody found in or induced in the rat is related in function and reaction to immunoglobulin E (reagin or IgE) found in the human. The correlation between homocytotropic antibody in the rat and IgE in the human has been established through the common effects obtained from chemical reactions, immunological reactions and drug responses in the two species hosting those antibodies. In the human, reagin is the antibody responsible for atopic immediate hypersensitive reactions. In the rat, the homocytotropic antibody is responsible for atopic immediate hypersensitive reactions.

In theory, reagin, influences the cell membrane of a mast cell by reacting with an antigen, to initiate the reaction(s) within the mast cell which ultimately releases a mediator such as Bradykinin, SRS-A (slow reacting substance-A), histamine and other unknown substances. The mediator effects a change in surrounding cell wall permeability permitting a rapid change in flow or exudance of mediator(s) from the cells, resulting in an allergic attack symptom. The various methods commonly employed to relieve the symptoms of allergic attack, none of which are considered to be quite acceptable, are to (1) avoid attack by the antigen, (2) block the production of antibody with an immunosuppressant, (3) block the action of the mediators on the cell under attack by administration of anti-histaminics, anti-5-hydroxy-tryptamines(5-HT) or anti-inflammatories, or (4) stimulate the cell under attack to negate the action of the mediator through the action of bronchodilators such as Isuprel ® or a Xanthine.

A compound typifying anti-allergic activity by blocking reaction(s) within the mast cells, thereby preventing the production and release of mediators, is disodium cromoglycate. (INTAL ®).

DESCRIPTION OF THE INVENTION

In accordance with this invention, there is provided a process for preventing the release of pharmacological mediators from an immediate hypersensitivity reaction between reaginic type antibodies and an antigen, thereby preventing the symptoms manifest in bronchial asthma, seasonal pollinosis, allergic rhinitis, urticaria, allergic conjunctivitis, food allergy and anaphylactoid reactions of a sensitized animal, which comprises prophylactically administering to said animal an effective amount of a compound of the formula:

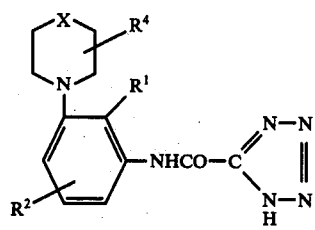

in which $R^1$ is —CN or —CONH$_2$;

$R_2$ is hydrogen, lower alkyl, lower alkoxy, halo, polyhalo(lower)alkyl, lower alkyl carbonyl or carb(lower)alkoxy;

X is —CH$_2$—, —O— or

where $R^3$ is lower alkyl; and $R^4$ is hydrogen or lower alkyl;

or a pharmaceutically acceptable salt thereof.

In accordance with the compound aspect of this invention, there is provided a group of N-aromatic 1H-(or 2H) tetrazole-5-carboxamide derivatives of the following structural formulae:

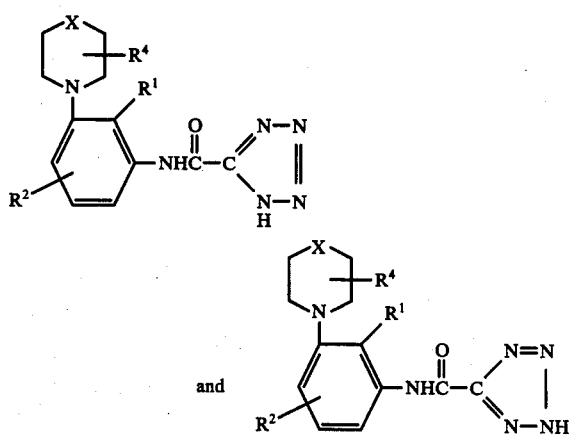

in which $R^1$ is —CN or CONH$_2$;

$R^2$ is hydrogen, lower alkyl, lower alkoxy, halo, polyhalo(lower)alkyl, lower alkyl carbonyl or carb(lower)alkoxy;

X is —CH$_2$—, —O— or

where $R^3$ is lower alkyl; and
$R^4$ is hydrogen or lower alkyl;
or a pharmaceutically acceptable salt thereof.

In addition, this invention provides a process for the production of N-aromatic and N-heterocyclic 1H-(or 2H) tetrazole-5-carboxamide derivatives in general. Basically, the process involves the reaction of an amine $ANH_2$, where A represents the aromatic or heterocyclic moiety, with a 1-protected-1H-tetrazole-5-carbonyl chloride followed by deprotection (hydrogenolysis) and conversion to a pharmaceutically acceptable non-toxic salt as desired.

More specifically, the process involved in producing the N-aromatic and N-heterocyclic 1H-(or 2H) tetrazole-5-carboxamide derivatives may be described as a process which comprises:

(a) reacting an N-protected oxamic acid ester with $PCl_5$ in the presence of an acid acceptable to obtain the imidochloride

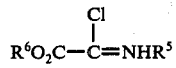

in which $R^6$ is lower alkyl and $R^5$ is a protecting group;

(b) cyclizing the imido-chloride with hydrazoic acid to produce the lower alkyl ester of 1-$R^5$-5-carboxy-1H-tetrazole;

(c) saponifying said ester to obtain an alkali metal salt of said tetrazole;

(d) converting said tetrazole salt to the 5-chlorocarbonyl1-$R^5$-1H-tetrazole by reaction with a chlorinating agent;

(e) reacting said 5-chlorocarbonyl-1-$R^5$-1H tetrazole with an amine of the formula $ANH_2$;

(f) removing the 1-$R^5$ group from the product of step(e) to obtain the N-substituted-1H-(or 2H) tetrazole-5-carboxamide of the formula:

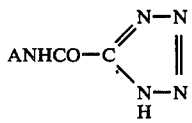

in which

A is a member selected from the group consisting of 2-thiazolyl, 2-pyridyl, 6-(lower)alkyl-2-pyridyl, 3-cyano-2-pyridyl, 3-pyridyl, 4-pyridyl, 2-pyrimidinyl, 2-pyrazinyl, α-naphthyl, β-naphthyl, phenyl, 2,6-dichlorophenyl, and substituted phenyl moieties having from one to three substituents in any of the 2,3,4 and 5 positions of the phenyl ring, independently selected from the group consisting of lower alkyl, lower alkylsulfinyl, lower alkoxy, hydroxy(lower)alkoxy, 2-(lower alkoxy oxalyloxy)ethoxy, N-mono- and di-lower alkyl amino (lower)alkoxy, halo, sulfamyl, polyhalo(lower)alkyl, carbamyl, N-lower alkylcarbamyl, carboxy, lower alkylcarbonyl, cyano, carb(lower)alkoxy, phenoxy(lower)alkoxy, lower alkoxyoxalamido, lower alkoxyoxalamidophenoxy and

where $R^8$ and $R^7$, independently represent hydrogen, lower alkyl, lower alkenyl, lower alkynyl, cycloalkyl of 5 or 6 carbon atoms, aralkyl of 7 to 9 carbon atoms, aryl of 6 to 10 carbon atoms or, $R^8$ and $R^7$, taken together with the nitrogen atom to which they are attached form a heterocyclic group selected from aziridinyl, azetidinyl, pyrrolidinyl, piperidine, piperazinyl, 4-lower alkylpiperazinyl, morpholino, thio morpholino and a ring substituted lower alkyl analogue of said heterocyclic group.

In the preceding paragraph, the definition of $R^8$ or $R^7$ as aralkyl of 7 or 8 carbon atoms is intended to embrace the benzyl and phenethyl radicals. The cycloalkyl groups of 5 or 6 carbon atoms embrace cyclopentyl as well as cyclohexyl. Where either $R^8$ or $R^7$ is hydrogen, undesired acylation of the amino group —$NHR^7$ is accomplished conventionally by protecting that group with a standard protecting group such as the trimethylsilyl group, which is readily removed upon completion of the reaction between the amine $ANH_2$ and the tetrazole-5-carbonyl chloride.

The chlorinating agent employed in step (d) of the process may be any conventional agent employed in the production of a carboxylic acid chloride such as $SOCl_2$, $PCl_5$, $PCl_3$, oxalyl chloride, and the like.

The term "lower" used throughout this application to modify alkyl, alkoxy, alkenyl, alkynyl, and the like, is intended to embrace those univalent aliphatic hydrocarbon radicals having 1 to 6 carbon atoms. The term "halo" is used to embrace chlorine, bromine, iodine and fluorine. The expression "pharmaceutically acceptable salts" is intended to embrace acid addition salts, where applicable as well as 1H-(or 2H) tetrazole alkali metal or amine salts. Examples of acids with which pharmaceutically acceptable non-toxic salts may be produced include both organic and inorganic acids such as hydrochloric, hydrobromic, sulfuric, phosphoric, methane sulfonic, nitric, p-toluene sulfonic, acetic, citric, maleic, succinic acid, and the like. The alkali metal or amine salts of the 1H-(or 2H) tetrazoles include salts of sodium, potassium, lower alkylamine, di(lower alkyl)amine, tri(lower alkyl)amine and the corresponding omega-hydroxy analogues (e.g. methylamine, ethylamine, propylamine, dimethylamine, diethylamine, dipropylamine, trimethylamine, triethylamine, tripropylamine, di(hydroxyethyl)amide, and the like) as well as more complex amines which are employed in depot administration, such as $N,N^1$-dibenzylethylenediamine, and the like. Furthermore, applicants intend throughout this application, by either structural presentation or by compound name referring to either the 1H- or 2H-tetrazole configuration of the final products, to embrace both of those tautomeric forms of the unsubstituted tetrazole nucleus.

The protecting group —$R^5$—employed in preparation of the 1H-tetrazole-5-carbonyl chloride intermediate is selected for its stability during reaction of the lower alkyl oximidoyl chloride with hydrazoic acid while possessing the attribute of easy removal after formation of the carboxamide product. Examples of such protecting groups are benzyl, 4-methoxybenzyl, 2,4-dimethoxybenzyl, 2,6-dimethoxybenzyl, 2,4,6-trimethoxybenzyl, trichloroethyl, and the like.

The preparation of the 1H-tetrazole-5-carboxylic acid lower alkyl esters is quite unique in itself and forms an additional aspect of this invention. Thus, applicants have discovered, unexpectedly, that a N-protected lower alkyl ester of oximidoyl chloride reacts with hydrazoic acid to afford the 1H-tetrazole-5-carboxylic acid lower alkyl esters and that the combination of the N-protecting group with the presence of a lower alkyl ester functional group in the intermediate imido chloride, cooperate in such manner as to direct the attack of hydrazoic acid in the desired fashion without interference by the ester function.

In that sense, applicants provide a process for producing 1H-tetrazole-5-carboxylic acid lower alkyl esters which comprises reacting a N-protected oxamic acid lower alkyl ester such as N-benzyloxamic acid ethyl ester with $PCl_5$ in the presence of an acid acceptor to afford the corresponding imidoyl chloride intermediate, which reacts with hydrazoic acid to yield the desired N-protected-1H-tetrazole-5-carboxylic acid esters.

In the formation of the 1H-tetrazole-5-carboxylic acid ester from the imido-chloride precursor, the reactant hydrazoic acid may be produced in situ from, for example, a metal azide, trimethylsilylazide or ammonium azide. It is intended, throughout this specification that the expression hydrazoic acid should be interpreted as encompassing the metal azides, trimethylsilylazide and ammonium azide.

The compounds of this invention relieve atopic allergic manifestations, when administered orally and parenterally to sensitized rats.

The technique employed to establish the anti-allergic activity of the 1H-tetrazole-5-carboxamide derivatives of this invention is reported in Immunology, vol. 16, pp. 749–760 (1969) and involves four male Charles River rats (200–250 grams body weight) per group to provide a control, a host for administration of a standard anti-allergic compound (disodium cromoglycate) and animals for the test compound. The rats were injected intracutaneously on their shaved backs with sera from rats immunized with egg albumin and pertussis vaccine. Twenty-four hours after the initial injections, the test compound is administered intraperitoneally or orally at a dosage level of 200 milligrams per kilogram host body weight or less. Five minutes later 1 milliliter of a 0.5 percent solution of Evans blue dye and 8 milligrams of egg albumin is injected intravenously. After 40 minutes, the animal is sacrificed and the bleb size on its back is measured. The mean bleb size for the animals administered the test compound is calculated and the percent inhibition is determined by comparison with the control animal.

Although the mechanism by which the compounds of this invention function is not absolutely known, applicants have found that the compounds of this invention, in a manner believed to be similar to the function of INTAL ®, block reaction(s) in the mast cell leading to the production and release of mediators.

The compounds of this invention permit the occurrence of a non-productive antigen-antibody interaction. They effectively block the IgE type reaction and have little or no effect on the other immunoglobulins such as IgG, IgM, IgA and IgD.

In other words, the compounds of this invention block the release of mediators commonly resulting from the antigen-antibody reaction as exemplified in a passive cutaneous anaphylaxis test (PCA) using rat homocytotropic antibody—a known correlate of human reaginic antibody.

By analogy to disodium cromoglycate and its activity correlation between standard test animals, domestic animals and man, the compounds of this invention have been established as anti-allergic agents suitable for the same uses at analogous doses and through the same routes of administration as INTAL ®.

Thus, there is provided herewith a method for suppressing allergic manifestations of atopic immediate sensitivity in warm-blooded, human and non-human animals, the latter including domesticated animals such as the mouse, rat, hamster, gerbil, dog, cat, sheep, goat, horse, cow, and the like, by administering an effective amount of one or more of the compounds disclosed in this application by oral, topical, parenteral, rectal, vaginal or inhalation routes. The compounds of this invention may be administered in conjunction with known compounds effecting anti-histaminic, anti-hypertensive, analgesic, central nervous system depressant, immunosuppressive, anti-serotonin, anti-Bradykinin or endocrinological responses. In addition, those conventional adjuvants known to the art may be combined with the anti-allergics of this invention to provide compositions and solutions for administrative purposes, although it is considered desirable and feasible to employ the anti-allergics as neat or pure compounds without additives other than for purposes of providing suitable pharmaceutical solution or liquid or vapor suspensions, the latter for use as inhalants.

The oral dose range lies from below 0.1 milligram per kilogram to about 50 milligrams per kilogram host body weight. As an inhalant the dose is from that of INTAL ®, (about 20 milligrams) to 1/20th that quantity administered as needed prior to attack. Thus the dosage contemplated for human use based upon the potency of the compounds administered lies from about 5 milligrams to 1 gram, preferably 50 milligrams to about 750 milligrams in unit dosage form to be administered when necessary and to the degree of the desired response, in single or plural doses under the guidance of a physician.

EXAMPLE I

N-[2-Cyano-3-(4-morpholinyl)phenyl]-1H-tetrazole-5-carboxamide

To a solution of 20.72 g. (0.1 mol.) of benzyloxamic acid ethyl ester and 9.89 g. (0.125 mol.) of pyridine in 95 ml. of methylene chloride is added 26.03 g. (0.125 mol.) of $PCl_5$ slowly through a Gooch tube at 30° C. or less. Stir 1 hour at room temperature, add 112 ml. of 1.78 molar hydrazoic acid in benzene, stir 1 hour at room temperature, and slowly bring to reflux. After 4½ hour of reflux, keep the reaction mixture over night at room temperature. The reaction mixture is poured into a cold $NaHCO_3$ solution, diethyl ether is added and separate the layers. The organic layer is washed again with a $NaHCO_3$ solution, with N HCl, with brine and dried with $CaCl_2$. Evaporation of the solvent gives 22.46 g. of oil which is distilled in a falling film molecular still at 135° C. and 0.15 mm, giving 11.12 g. of product. The oil is crystallized from diethyl ether-pentane to give 6.88 g. of 1-benzyl-1H-tetrazole-5-carboxylic acid ethyl ester, m.p. 51°–55° C.

Anal. Calcd. for $C_{11}H_{12}N_4O_2$: C, 56.89; H, 5.21; N, 24.13. Found: C, 56.58; H, 5.11; N, 24.13.

The ethyl ester (11.61 g., 0.05 mol.) is dissolved in 60 ml. of warm absolute ethyl alcohol. Addition of 3.96 g. (0.06 mol.) of KOH in 7 ml. of water causes crystallization of the potassium salt. The mixture is kept at room temperature over night, filtered, and the filter cake is washed with cold absolute ethyl alcohol and diethyl ether, giving 11 g. of 1-benzyl-1H-tetrazole-5-carboxylic acid potassium salt.

Anal. Calcd. for $C_9H_7KN_4O_2$: C, 44.61; H, 2.91; N, 23.13. Found: C, 44.26; H, 2.91; N, 23.27.

The potassium salt (7.27 g., 0.03 mol.) and 1.5 ml. of pyridine are stirred at 6° C. in 135 ml. of benzene, and 25 ml. of oxalyl chloride is rapidly added. After stirring ½ hour at 15° C. the mixture is stripped at 15° C., and scrubbed with two portions of 130 ml. of benzene at 15° C. giving a crude mixture of 1-benzyl-1H-tetrazole-5-carbonyl chloride. This preparation of the acid chloride is kept cold and used immediately for acylation.

The crude acid chloride (0.03 mol.) from above is dissolved in 130 ml. $CH_2Cl_2$ and poured into a solution of 2-amino-6-(4-morpholinyl)benzonitrile (6.10 g., 0.03 mol.) and 2.73 g. of pyridine in 130 ml. of $CH_2Cl$ at 5°-10° C. The solution is allowed to come to room temperature during 2 hours, and then wash twice with water, with brine, and dry with $CaCl_2$. The solution is evaporated to dryness giving 10.7 g. (m.p. 176°-180° C.) of a white solid which is crystallized from 100 ml. of acetonitrile, giving 7.65 g. of 1-benzyl-N-[2-cyano-3-(4-morpholinyl)phenyl]-1H-tetrazole-5-carboxamide as white crystals, m.p. 184°-187° C.

Anal. Calcd. for $C_{20}H_{19}N_7O_2$: Found: C, 61.68; H, 4.92; N, 25.18. C, 61.57; H, 4.78; N, 25.11.

The N-benzyl derivative above (1.95 g., 0.005 mol.) is dissolved in warm acetic acid and 0.9 g. of 10% Pd/C is added. The mixture is hydrogenated at 35 lbs. over night, and the mixture is filtered and the cake is washed with hot acetic acid. The filtrate is stripped to dryness and the residue is triturated with a warm solution of 10 ml. concentrated ammonium hydroxide in 60 ml. of water. The mixture is filtered and the filtrate is acidified to pH 2 with concentrated HCl. The acidified mixture is kept in ice for 2 hours, filtered, and the white product is dried. Crystallization of the product from acetonitrile gives 0.42 g. of N-[2-cyano-3-(4-morpholinyl)phenyl]-1H-tetrazole-5-carboxamide, m.p. 253°-256° C. (dec.).

Anal. Calcd. for $C_{13}H_{13}N_7O_2$: C, 52,17; H, 4.38; N, 32.76. Found: C, 52.04; H, 4.34; N, 32.76.

The title compound exhibited 60 percent inhibition of the mean bleb size when administered orally at 0.1 milligrams per kilogram and 97% inhibition when administered orally at 50 milligrams/kilogram host body weight in accordance with the rat PCA test described, supra.

EXAMPLE II

N-[2-Cyano-3-(1-piperidinyl)phenyl]-1H-tetrazole-5-carboxamide

In a manner similar to Example I, 1-benzyl-1H-tetrazole-5-carbonyl chloride is condensed with 2-amino-6-(1-piperidinyl)benzonitrile to give 1-benzyl-N-[2-cyano-3-(1-piperidinyl)phenyl]-1H-tetrazole-5-carboxamide.

In a manner similar to Example I and benzyl group is hydrogenolyzed from the above tetrazole giving the title compound.

EXAMPLE III

N-[2-Cyano-3-(4-methyl-1-piperazinyl)phenyl]-1H-tetrazole-5-carboxamide

In a manner similar to Example I, 1-benzyl-1H-tetrazole-5-carbonyl chloride is condensed with 2-amino-6-(4-methyl-1-piperazinyl)benzonitrile to give 1-benzyl-N-[2-cyano-3-(4-methyl-1-piperazinyl)phenyl]-1H-tetrazole-5-carboxamide.

In a manner similar to Example I the benzyl group is hydrogenolyzed from the above tetrazole giving the title compound.

EXAMPLE IV

N-[2-carbamoyl-3-(4-morpholinyl)phenyl]-1H-tetrazole-5-carboxamide

In a manner similar to Example I, 1-benzyl-1H-tetrazole-5-carbonyl chloride is condensed with 2-amino-6-(4-morpholinyl) benzamide to give 1-benzyl-N-[2-carbamoyl-3-(4-morpholinyl)phenyl]-1H-tetrazole-5-carboxamide.

In a manner similar to Example I the benzyl group is hydrogenolyzed from the above tetrazole giving the title compound.

EXAMPLE V

N-[2-Cyano-3-(2-methyl-4-morpholinyl)phenyl]-1H-tetrazole-5-carboxamide

In a manner similar to Example I, 1-(4-methoxybenzyl)-1H-tetrazole-5-carbonyl chloride is condensed with 2-amino-6-(2-methyl-4-morpholinyl)benzonitrile to give 1-(4-methoxybenzyl)-N-[2-cyano-3-(2-methyl-4-morpholinyl)phenyl]-1H-tetrazole-5-carboxamide.

By a process similar to those revealed by D. L. Lee and H. Rappaport in J. Org. Chem., 40, 3491(1975) and F. Weygand, et al., in Chem. Ber. 101, 3623(1968) the 4-methoxybenzyl group is removed from the above tetrazole.

The corresponding thio morpholino analogue is prepared by the method of Example V employing the 4-methoxybenzyl protecting group to ultimately obtain N-[2-Cyano-3-(thio morpholino)phenyl]-1H-tetrazole-5-carboxamide.

The amine reactants $ANH_2$ are generally known compounds or they may be readily produced by known methods. Typical examples of the production of various applicable amines may be found in copending U.S. applications Ser. Nos. 620,626, filed Oct. 3, 1975 and 542,465, filed Jan. 20, 1975, the disclosures of said applications being incorporated herein for the purpose of illustrating the various intermediates involved.

The amines —$ANH_2$— listed below readily enter into reaction with an N -protected -1H-tetrazole-5-carbonyl chloride to yield the final products listed below:

| $ANH_2$ | Final Product |
| --- | --- |
| 2-aminothiazole | N-[2-thiazolyl]-1H-tetrazole-5-carboxamide |
| 2-aminopyridine | N-[2-Pyridyl]-1H-tetrazole-5-carboxamide |
| 2-aminonicotinonitrile | N-[3-cyano-2-pyridyl]-1H-tetrazole- |

-continued

| ANH₂ | Final Product |
|---|---|
| | 5-carboxamide |
| 2-aminopyrimidine | N-[2-pyrimidinyl]-1H-tetrazole-5-carboxamide |
| 4-aminopyridino | N-[4-pyridyl]-1H-tetrazole-5-carboxamide |
| 3-aminopyridine | N-[3-pyridyl]-1H-tetrazole-5-carboxamide |
| 2-amino-6-picoline | N-[2-(6-methyl)pyridyl-1H-tetrazole-5-carboxamide |
| 2-aminopyrazine | N-[2-pyrazinyl]-1H-tetrazole-5-carboxamide |
| Aniline | N-[2-pyrazinyl]-1H-tetrazole-5-carboxamide |
| 2-aminobenzoic acid | N-[2-carboxyphenyl]-1H-tetrazole-5-carboxamide |
| 2-aminobenzamide | N-[2-carbamoylphenyl]-1H-tetrazole-5-carboxamide |
| 2-cyanoaniline | N-[2-cyanophenyl]-1H-tetrazole-5-carboxamide |
| 2-methylaniline | N-[2-methylphenyl]-1H-tetrazole-5-carboxamide |
| 2-methoxyaniline | N-[2-methoxyphenyl]-1H-tetrazole-5-carboxamide |
| 3-methoxyaniline | N-[3-methoxyphenyl]-1H-tetrazole-5-carboxamide |
| 3-trifluoromethylaniline | N-[3-trifluoromethylphenyl]-1H-tetrazole-5-carboxamide |
| 3-fluoroaniline | N-[3-fluorophenyl]-1H-tetrazole-5-carboxamide |
| 3-methylaniline | N-[3-methylphenyl]-1H-tetrazole-5-carboxamide |
| 4-aminobenzamide | N-[4-carbamoylphenyl]-1H-tetrazole-5-carboxamide |
| 4-methoxyaniline | N-[4-methoxyphenyl]-1H-tetrazole-5-carboxamide |
| 4-methylaniline | N-[4-methylphenyl]-1H-tetrazole-5-carboxamide |
| 2-amino-6-methoxybenzamide | N-[2-carbamoyl-3-methoxyphenyl]-1H-tetrazole-5-carboxamide |
| 2-amino-6-methoxy benzoic acid | N-[2-carboxy-3-methoxyphenyl]-1H-tetrazole-5-carboxamide |
| 2-cyano-3-methoxyaniline | N-[2-cyano-3-methoxyphenyl]-1H-tetrazole-5-carboxamide |
| 2-amino-6-chlorobenzamide | N-[2-carbamoyl-3-chlorophenyl]-1H-tetrazole-5-carboxamide |
| 2-amino-6-phenoxyethoxybenzamide | N-[2-carbamoyl-3-phenoxyethoxyphenyl]-1H-tetrazole-5-carboxamide |
| 2-amino-5-methoxy benzoic acid | N-[2-carboxy-4-methoxyphenyl]-1H-tetrazole-5-carboxamide |
| 2-amino-5-chlorobenzamide | N-[2-carbamoyl-4-chlorophenyl]-1H-tetrazole-5-carboxamide |
| 2-amino-4-methoxybenzamide | N-2-carbamoyl-5-methoxyphenyl]-1H-tetrazole-5-carboxamide |
| 5-chloro-2-sulfamoylaniline | N-[5-chloro-2-sulfamoylphenyl]-1H-tetrazole-5-carboxamide |
| 2,6-dichloroaniline | N-[2,6-dichlorophenyl]-1H-tetrazole-5-carboxamide |
| 4-(4-ethoxycarbamidophenoxy)aniline | N-[4-(4-ethoxycarbamidophenoxy)phenyl]-1H-tetrazole-5-carboxamide |
| 2-amino-6-ethoxybenzamide | N-[2-carbamoyl-3-ethoxyphenyl]-1H-tetrazole-5-carboxamide |
| 2-amino-6-propoxybenzamide | N-[2-carbamoyl-3-propoxyphenyl]-1H-tetrazole-5-carboxamide |
| 2-amino-6-isopropoxybenzamide | N-[2-carbamoyl-3-isopropoxyphenyl]-1H-tetrazole-5-carboxamide |
| 2-amino-6-n-butoxybenzamide | N-[2-carbamoyl-3-n-butoxyphenyl]-1H-tetrazole-5-carboxamide |
| 2-naphthylamine | N-[2-naphthyl]-1H-tetrazole-5-carboxamide |
| 1-naphthylamine | N-[1-naphthyl]-1H-tetrazole-5-carboxamide |
| 3,4,5-trimethoxyaniline | N-[3,4,5-trimethoxyphenyl]-1H-tetrazole-5-carboxamide |
| 2-amino-6-methoxy-N-methylbenzamide | N-[2-N-methylcarbamoyl-3-methoxyphenyl]-1H-tetrazole-5-carboxamide |
| 2-amino-6-(2-dimethylaminoethoxy)benzamide | N-[2-carbamoyl-3-(2-dimethylaminoethoxy)phenyl]-1H-tetrazole-5-carboxamide |
| 4,5-dimethylanthranilic acid | N-[2-carboxy-4,5-dimethylphenyl]-1H-tetrazole-5-carboxamide |
| 2-amino-4,5-dimethylbenzamide | N-[2-carbamoyl-4,5-dimethylphenyl]1H-tetrazole-5-carboxamide |
| 2-acetyl-3-methoxyaniline | N-2-acetyl-3-methoxyphenyl]-1H-tetrazole-5-carboxamide |
| 2-amino-6-(2-hydroxypropyl)benzamide | N-[2-carbamoyl-3-(2-hydroxypropyl)phenyl]-1H-tetrazole-5-carboxamide |
| 2-amino-4,6-dimethoxybenzamide | N-[2-carbamoyl-3,5-dimethoxyphenyl]1H-tetrazole-5-carboxamide |
| 2-amino-6-(2-hydroxyethoxy)benzamide | N-[2-carbamoyl-3-(2-hydroxyethoxy)phenyl]-1H-tetrazole-5-carboxamide |
| 2-amino-6-benzyloxybenzamide | N-[2-carbamoyl-3-benzyloxyphenyl]-1H-tetrazole-5-carboxamide |
| 4-chloroaniline | N-[4-chlorophenyl)-1H-tetrazole-5- |

-continued

-continued

| ANH₂ | Final Product |
|---|---|
| 4-dimethylaminoaniline | carboxamide<br>N-[4-dimethylaminophenyl]-1H tetrazole-5-carboxamide |
| 2-amino-6-dimethylamino-benzamide | N-[2-carbamoyl-3-dimethylamino-phenyl]-1H-tetrazole-5-carboxamide |

What is claimed is:

1. An anti-allergy compound of the formula:

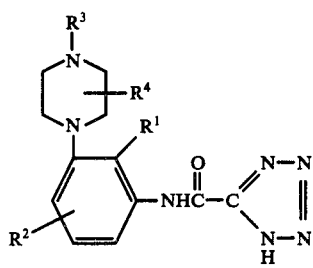

in which
R¹ is —CN or —CONH₂;
R² is hydrogen, lower alkyl, lower alkoxy, halo, polyhalo(lower)alkyl, lower alkyl carbonyl or carb(lower)alkoxy;
R³ is lower alkyl; and
R⁴ is hydrogen or lower alkyl;
or a pharmaceutically acceptable salt thereof.

2. A compound of claim 1 of the formula:

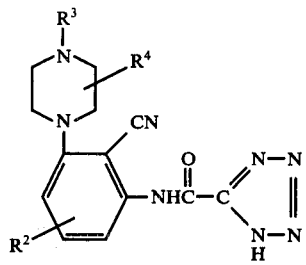

in which
R² is hydrogen, lower alkyl, lower alkoxy, halo, polyhalo(lower)alkyl, lower alkyl carbonyl or carb(lower)alkoxy;
R³ is lower alkyl; and
R⁴ is hydrogen or lower alkyl;
or a pharmaceutically acceptable salt thereof.

3. A compound of claim 1 of the formula:

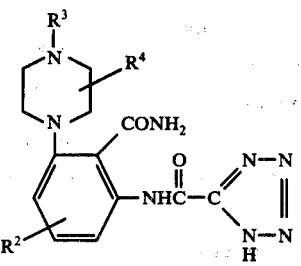

in which
R² is hydrogen, lower alkyl, lower alkoxy, halo, polyhalo(lower)alkyl, lower alkyl carbonyl or carb(lower)alkoxy;
R³ is lower alkyl; and
R⁴ is hydrogen or lower alkyl;
or a pharmaceutically acceptable salt thereof.

4. The compound which is N-[2-cyano-3-(4-methyl-1-piperazinyl)phenyl]-1H-tetrazole-5-carboxamide.